United States Patent
Mears

[19]

[11] Patent Number: 6,059,797
[45] Date of Patent: May 9, 2000

[54] SELF-DISPOSING LIGATING BAND DISPENSER

[75] Inventor: Eric L. Mears, Duluth, Ga.

[73] Assignee: Ensurg, Inc., Norcross, Ga.

[21] Appl. No.: 09/098,945

[22] Filed: Jun. 17, 1998

[51] Int. Cl.$^7$ .................................................. A61B 17/10
[52] U.S. Cl. ........................ 606/140; 606/139; 606/141
[58] Field of Search .................................. 606/140, 141, 606/139, 148, 151

[56] References Cited

U.S. PATENT DOCUMENTS

| | | | |
|---|---|---|---|
| 3,760,810 | 9/1973 | Van Hoorn | 128/326 |
| 3,911,923 | 10/1975 | Yoon | 128/303 A |
| 4,226,239 | 10/1980 | Polk et al. | 128/303 A |
| 4,257,419 | 3/1981 | Göltner et al. | 128/303 A |
| 4,990,152 | 2/1991 | Yoon | 606/140 |
| 5,207,690 | 5/1993 | Rohrabacher et al. | 606/135 |
| 5,269,789 | 12/1993 | Chin et al. | 606/140 |
| 5,320,630 | 6/1994 | Ahmed | 606/140 |
| 5,356,416 | 10/1994 | Chu et al. | 606/140 |
| 5,398,844 | 3/1995 | Zaslavsky et al. | 221/208 |
| 5,462,559 | 10/1995 | Ahmed | 606/140 |
| 5,507,797 | 4/1996 | Suzuki et al. | 606/140 |
| 5,569,268 | 10/1996 | Hosoda | 606/140 |
| 5,624,453 | 4/1997 | Ahmed | 606/140 |
| 5,681,328 | 10/1997 | Lamport et al. | 606/140 |
| 5,697,940 | 12/1997 | Chu et al. | 606/140 |
| 5,735,861 | 4/1998 | Peifer et al. | 606/139 |
| 5,857,585 | 1/1999 | Tolkoff et al. | 221/36 |

FOREIGN PATENT DOCUMENTS

WO9745060  12/1997  WIPO .

OTHER PUBLICATIONS

Directions for use Brochure for Speedband™ Multiple Band Ligator, Microvasive Boston Scientific Corporation, pp. 1–8, 1995.

*Primary Examiner*—Michael Buiz
*Assistant Examiner*—Lien Ngo
*Attorney, Agent, or Firm*—Sidley & Austin

[57] ABSTRACT

A self-disposing ligating band dispenser is formed of a member having predisposed windings, where the windings form a surface to support one or more expanded ligating bands. The wound member has a free portion which enables a properly oriented displacement of the free portion to effect the unwinding of the dispenser, and the dispensing of one or more stored ligating bands.

39 Claims, 4 Drawing Sheets

SELF-DISPOSING LIGATING BAND DISPENSER

FIELD OF THE INVENTION

The present invention relates to a ligating band dispenser, and in particular, to a ligating band dispenser which can sequentially dispense one of a plurality of expanded ligating bands.

BACKGROUND OF THE INVENTION

Ligation is a medical procedure in which, for example, an elastic ligating band, is placed about tissue to prevent fluid flow therethrough. Where a ligating band is placed about, for example, a ballooning varix, polyp, hemorrhoid, or precancerous lesion, a contracted ligating band induces fusion and healing in the base tissue and subjects the ligated tissue to necrosis. The necrotic tissue eventually separates from the surrounding tissue and passes into the human system. Alternatively, ligation may also be used for purposes of sterilization, wherein a ligating band may be placed over a folded loop portion of a Fallopian tube or a vas deferens to prevent the passage of internal reproductive fluids.

Means for delivering ligating bands, or ligating band dispensers, take various forms. One such form is a dedicated ligating band dispenser instrument which has a dispensing portion at a distal end, an actuating mechanism at a proximal end, and a typically rigid shaft therebetween. These instruments are useful for ligating tissue in which the user has access to the tissue to be ligated, e.g., tissue exposed through an invasive surgical procedure.

In contrast, ligating band dispensers may be positioned on the distal tip of an endoscope or a laparoscope. An endoscope is a conventional medical device used for viewing, exploring, and delivering therapies to internal regions of a patient. A laparoscope is a specialized endoscope for viewing a patient's peritoneal cavity. Unlike dedicated ligating band dispensing instruments, an endoscope allows minimally invasive exploration of regions which would otherwise require more significant surgical procedures.

FIGS. 1 and 2 illustrate a conventional endoscope. Endoscope 10 has a control portion 12 and an insertion portion 14 terminating at insertion tip 16. Insertion portion 14 is of such a length to permit access to internal regions of a patient.

FIG. 2 illustrates the face of insertion tip 16. A number of channels extend from the control portion 12 to the insertion tip 16, where the channels terminate in functional outlets 18–26. For the purposes of this example, outlet 18 is a light source; outlet 20 is a wide-field image sensing device, which transmits a video or fiber optic signal to a coupled monitor or eyepiece (not shown) at control portion 12; outlet 22 enables the delivery of a stream of water or air for clearing the image receiving device or flushing an internal bodily region; and outlet 24 is an outlet to a working (or biopsy) channel. Inlet 28 of the working channel can be coupled to a suction device or a lavage fluid source (not shown) or can receive various medical instrumentation (not shown) for passage through the working channel and outlet 24. Optional outlet 26, for larger diameter endoscopes, is an outlet for a second working channel. A second working channel allows additional operations in a manner consistent with the working channel described above.

For a ligation procedure, a ligating band dispenser, mounted on insertion tip 16 of a hosting endoscope 10, is inserted into a patient, for example, through the mouth, to observe certain internal regions. A user navigates the insertion tip 16 in accordance with images produced by the image-sensing device of outlet 20. Once tissue has been targeted for ligation, the distal end of the dispenser is positioned adjacent to the targeted tissue. The user applies a vacuum to the appropriate outlet of insertion tip 16 (e.g., outlet 24), or passes instrumentation (e.g., forceps) through the work channel and outlet 24, to draw the targeted tissue into a volume defined by the inner periphery of the dispenser.

The user then dispenses a ligating band (two dispensers and their dispensing mechanisms are discussed in greater detail below). Upon dispensing a ligating band, the dispensed ligating band attempts to assume its non-expanded dimensions. As the subject tissue is positioned within the inner periphery of the ligating band, constriction of the band effectively ligates the subject tissue. The applied suction is ceased, and the insertion tip 16 is moved away from the ligated tissue and further exploration may be undertaken, if necessary.

Conventional endoscope ligating band dispensers commonly employ dispensing mechanisms which unnecessarily complicate a ligating procedure. Two examples of conventional mechanisms include a dispenser having a plurality of draw strings 1002 which are individually coupled to each of the stored ligating bands 1000 (FIG. 3), and a dispenser having a mechanically actuated housing which engages and requires movement of all stored ligating bands 1000 for each dispensing operation (FIG. 4).

In reference to FIG. 3, draw strings 1002 extend from each ligating band 1000 and around the distal end of the dispenser before extending proximally through the work channel of a receiving endoscope 10. Application of a proximally-directed force to a single draw string 1002 effects distal movement and dispensing of a coupled ligating band 1000.

As shown, each ligating band 1000 must be individually and properly coupled to at least one draw string 1002 to allow band control. As the number of stored ligating bands 1000 increase, the number of draw strings 1002, and the criticality of their placement, increases. The draw strings 1002 must be optimally positioned to ensure reliable dispensing of a distal-most ligating band, to avoid obstruction of the image sensing device of the hosting endoscope, and to avoid filling the volume defined by the dispenser and effectively decreasing the tissue capacity of the dispenser. Understandably, the construction of this dispenser requires considerable care and is necessarily labor intensive.

Referring to FIG. 4, another conventional dispenser example includes a mechanically actuated housing having a movable inner element 1008 and a fixed outer element 1010. Outer element 1010 carries a plurality of expanded ligating bands 1000, excepting the distal-most ligating band 1000a, which is carried by inner element 1008. For dispensing ligating band 1000a, element 1008 is drawn proximally, causing the distal-most ligating band 1001a to be released when inner element 1008 is pulled within outer element 1010. During such movement, the remaining ligating bands 1000 are displaced by shoulders 1012 so that when inner element 1008 returns distally, ligating bands 1000 are distally advanced.

This dispenser requires an applied dispensing force having a magnitude sufficient to not only dispense a single ligating band but also distally displace the remaining stored ligating bands in preparation for a next ligation. As the number of stored ligating bands increase, the force necessary to move the ligating bands as a group also increases.

Consequently, a user may experience some level of awkwardness during a procedure due to the force which may be necessary to dispense one or more ligating bands. Of further concern, this dispenser requires a number of working components to effect the dispensing of a ligating band, thus likely increasing the costs of the dispenser (i.e., assembly and materials) and functionally increasing the opportunity for a device malfunction.

Consequently, a need exists for a simple ligating band dispenser which offers safe, reliable, cost effective delivery of multiple ligating bands.

SUMMARY OF THE INVENTION

The present invention is directed to a ligating band dispenser. According to one aspect of the present invention, a ligating band dispenser is provided having a generally tubular self-disposing member, wherein an outer periphery is suitable to support at least one ligating band.

Accordingly to another aspect of the present invention, a ligating band dispenser is disclosed which is formed of a spirally wound element, wherein an outer periphery defined by the spirally wound element is suitable to support at least one ligating band. The element terminates in a free portion which allows control over the dispenser, and specifically, allows the dispenser to be unwound in a predetermined manner to selectively dispense each of the stored ligating bands.

In operation, a ligating procedure utilizing such a dispenser would generally include at least positioning a ligating band dispenser on a distal end of an insertion portion of an endoscope. The ligating band dispenser should support at least one ligating band. The insertion portion, including the dispenser, is then inserted into a patient and navigated to a desired tissue site. Adjacent to the tissue site, tissue which is to be ligated is drawn within a volume defined by the dispenser. A user then controls the free portion of the self-disposing member to effect an unwinding of the member sufficient to dispense a ligating band.

An object of the present invention is to provide a ligating band dispenser having simple, accurate functionality to independently and sequentially dispense one or more ligating bands.

Another object of the present invention is to provide a ligating band dispenser having a minimal number of working components to effect the dispensing of a ligating band.

Another object of the present invention is to provide a ligating band dispenser which secures at least one stored ligating band up to the time of dispensing, to prevent an unintentional or premature release.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Figure 1:
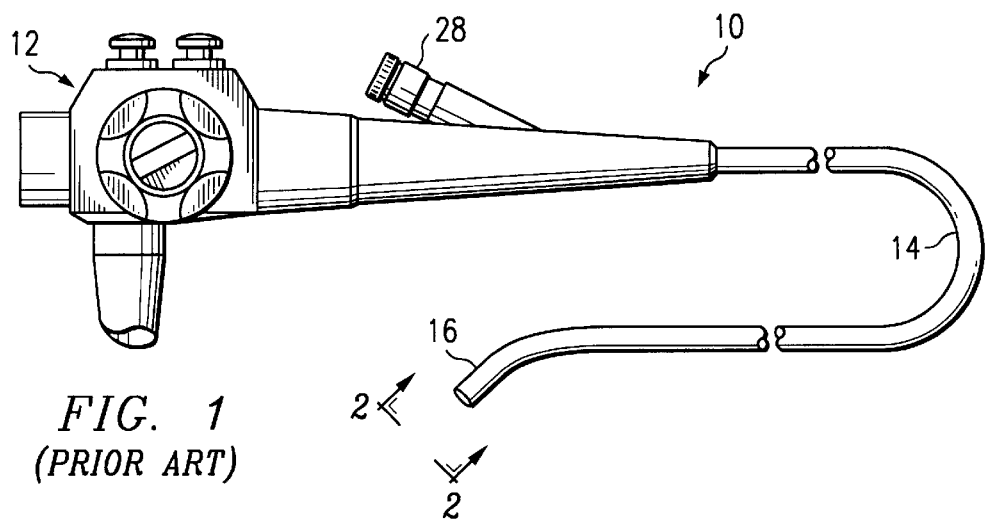
FIG. 1 illustrates a conventional endoscope device.
Figure 2:
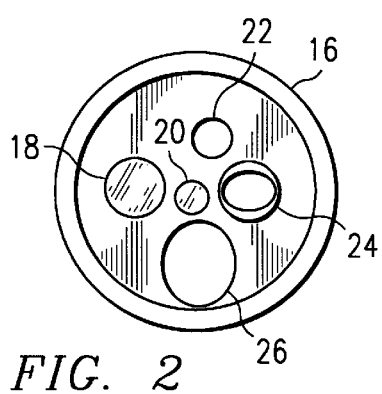
FIG. 2 is a view along line 2—2 of the insertion tip of the endoscope device of FIG. 1.
Figure 3:
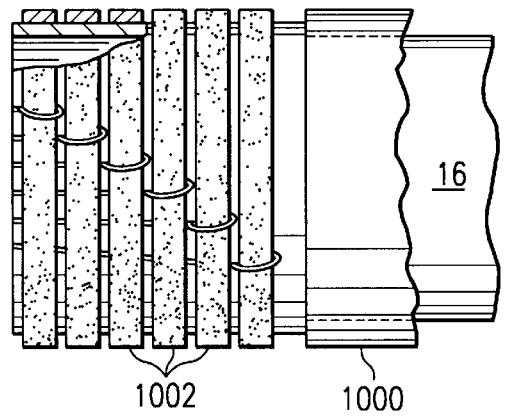
FIG. 3 illustrates a conventional ligating band dispenser.
Figure 4:
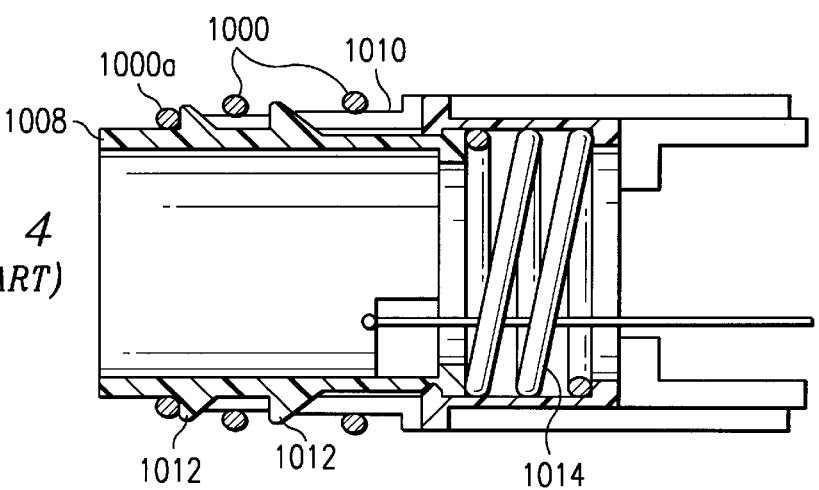
FIG. 4 illustrates a conventional ligating band dispenser.
Figure 5A:
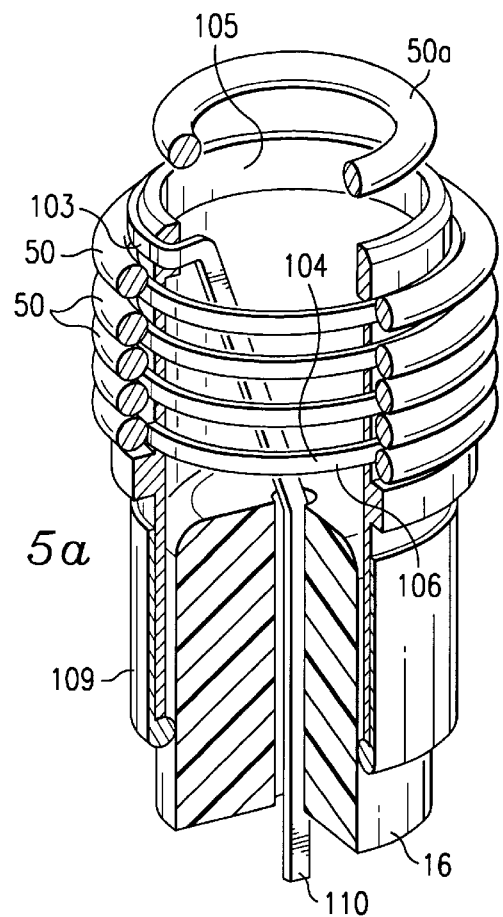
FIGS. 5a–5c are partial sectional views of a generalized ligating band dispenser in accordance with the present invention having differing control mechanisms.
Figure 5B:
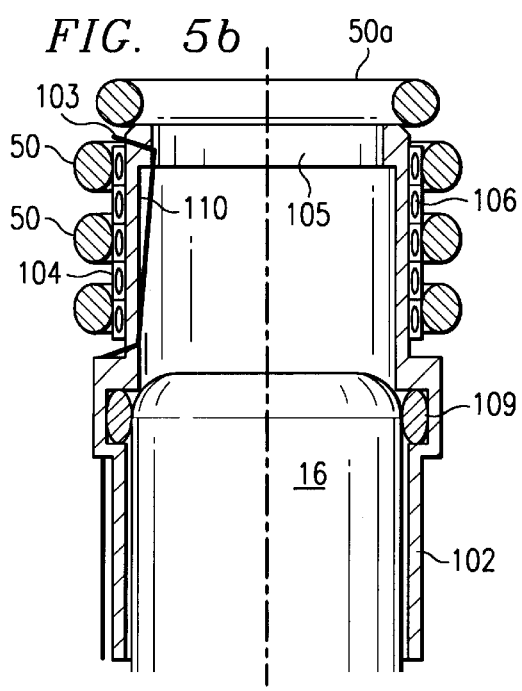
Figure 5C:
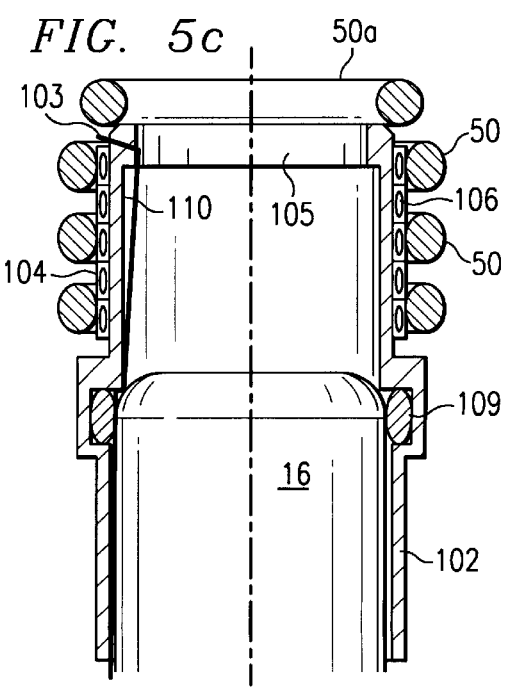

FIGS. 5a–5c illustrate ligating band dispenser 100 operatively positioned on insertion tip 16 of a hosting endoscope. Dispenser 100 includes sleeve 102 which supports self-disposing member 104. Member 104 is initially a hollow body with is formed so as to unravel, or unwind, in a predetermined helical pattern. An outer periphery of member 104 supports one or more ligating bands 50, where member 104 is resistant to circumferential compression. When dispenser 100 is fully unwound, dispenser 100 consists of a single, continuous filament (or member) 106, which will be further described in the context of each of the embodiments below.

Figure 6A:
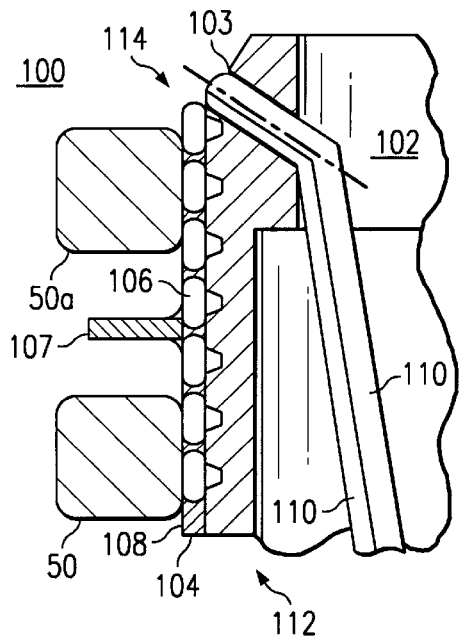
FIGS. 6a–6d are partial sectional views of a first, a second, a third, and a fourth embodiment, respectively, of the ligating band dispenser generally illustrated in FIGS. 5a–5c.

FIG. 6a illustrates a first embodiment of member 104. Filament 106 is a single or stranded filament, for example, a Teflon® filament (DuPont Corporation, Wilmington, Delaware) having an approximately 0.5 mm diameter. Filament 106 is wound from a proximal end 112 of member 104 to a distal end 114 and has a free portion 110. So that member 104 forms a unitary body, each individual winding of filament 106 is bonded to an adjacent winding using material 108. FIG. 6a shows member 104 formed of a single wound filament; however, it shall be understood that member 104 may be formed of a plurality of wound filaments 106, where it is preferred (although not required) that each of the filaments 106 do not intersect throughout their winding.

Material 108 is preferably friable which maintains filament 104 in a predetermined spiral but allows filament 106 to come free when a prescribed force is applied to free portion 110 of filament 106. Material 108 has a preferred thickness equal to or less than the diameter of filament 106. More preferably, the thickness of material 108 is between three-quarters and one-half the effective diameter of filament 106. Stops 107, also formed of material 108, may be formed between ligating bands 50 to prevent inadvertent or premature dispensing of ligating bands 50.

Material 108 may be a range of materials or substances which correspond to the material of filament 106. Specifically, for the specific example of filament 106 set forth above, material 108 may be a medical grade polymer, adhesive, or the like. In contrast, where filament 106 is a wire (for example, the second embodiment discussed below), material 108 may be an adhesive, solder, friction bond, weld, or the like. Depending on the nature of material 108, it may be used or applied in a conventional manner to join filament 106 with adjacent windings to form a substantially unitary body of member 104, for example, injection molded or extruded about positioned filament 106, heated, unified through a solvent, ultrasonically bonded, or any other known method.

Material 108 and filament 106 form an outer periphery which supports one or more ligating bands 50. An inner periphery of member 104 has a threaded surface which is defined by the helical windings of filament 106. When operatively positioned, the inner periphery of member 104 engages a complementary surface formed on an outer periphery of a distal portion of member 102. The threaded relationship of sleeve 102 and rotating member 104 precisely controls the rate of axial movement of member 104 relative to sleeve 102 and further prevents member 104 from being prematurely separated from sleeve 102 during a dispensing operation.

Figure 6C:
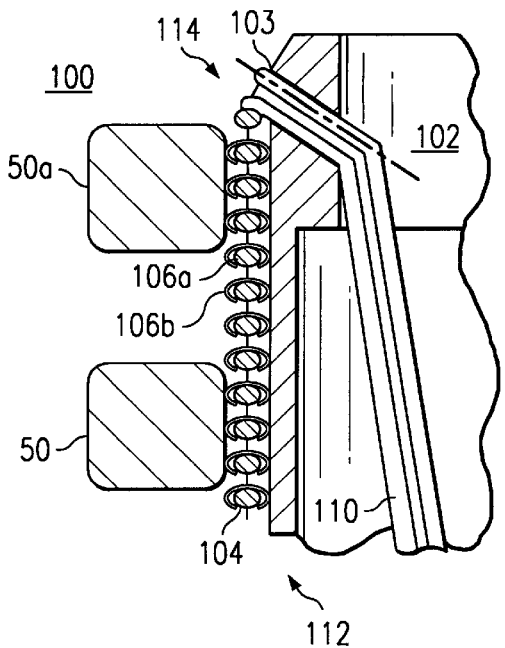
Figure 6B:
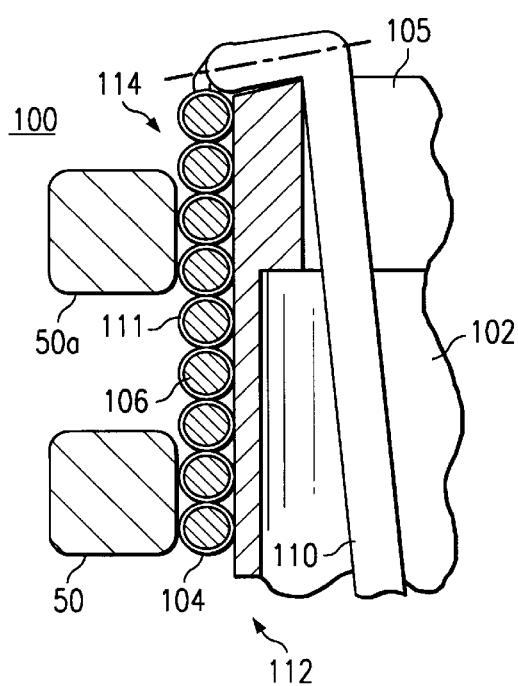
Figure 6D:
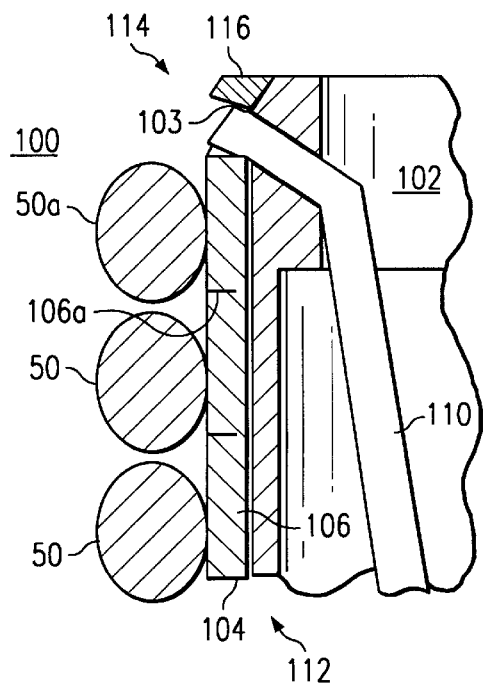

FIGS. 6a, 6c, and 6d illustrate sleeve 102 having aperture 103 to allow passage of the free portion 110 of filament 106 to the inner periphery of sleeve 102. Referring again to FIG. 5a, free portion 110 extends from the outer periphery of sleeve 102 to the volume defined by the inner periphery of sleeve 102 via aperture 103. For the illustrated device, free portion 110 continues proximally through a lumen (e.g., work channel) of hosting endoscope 10 to a controller (not shown) at control portion 12.

Alternative paths for free portion 110 are illustrated in FIGS. 5b and 5c. In FIG. 5b, filament 106 returns to the outer periphery of sleeve 102 through aperture 103 and then extends proximally, external to the insertion portion 14 of the hosting endoscope 10, to a controller at or about control portion 12. In FIG. 5c, filament 106 also extends external to the insertion portion 14 of the hosting endoscope 10 from dispenser 100 to a controller. Differing from FIG. 5b, however, filament 106 is interpositioned between sleeve 102 and insertion tip 16.

Returning to FIG. 6a, upon applying a predetermined, proximally-directed displacement to the free portion 110 of filament 106, member 104 is unwound and proximal end 112 (as well as any ligating bands 50 carried by member 104) is caused to advance distally. During application of the dispensing displacement, the sharp transition of aperture 103 relative to the outer periphery of sleeve 102 promotes the release of filament 106 from material 108. The rate of distal advancement of member 104 is determined by the pitch of the filament winding. In a preferred embodiment, the pitch of filament 106 is approximately 1–2 windings/mm.

Similar to the structure and functionality of dispenser 100 of the first embodiment, the following discussion is directed to a second, a third, and a fourth embodiment of dispenser 100. Like elements are referenced according to the first embodiment.

FIG. 6b illustrates the second embodiment, which is structurally similar to the embodiment of FIG. 6a. Specifically, member 104 is comprised of a helically wound wire 106, for example, formed from stainless steel or nitinol, wire 106 may or may not include insulative covering 111. The windings of wire 106 may be adhered or bonded together, using a medical grade adhesive or solder material or well-known ultrasonic or resistance welding processes, either continuously or intermittently. As another example, wire 106 may include a conventional insulation coating (not shown) which may be substantially unified between windings using a solvent treatment or heat. Alternatively, wire 106 may possess such rigidity to retain an original cylindrical shape and support one or more ligating bands 50 without having contiguous windings.

Sleeve 102 does not include aperture 103. In operation, the distal end of sleeve 102 and the distal end 114 of member 104 are largely aligned, and free portion 110 is allowed to circumvent opening 105 when a predetermined, proximally-directed displacement is applied to free portion 110. Consequently, the edge which defines opening 105 functions to release wire 106 from any bonds and/or to facilitate deformation of wire 106 with respect to its original shaping.

Functionally, unlike member 104 of FIGS. 6a, 6c, and 6d which rotates about sleeve 102 to effect axial displacement, the movement of member 104 of this embodiment relative to sleeve 102 is axial only (i.e., substantially no rotation) as wire 106 is unwound. Consequently, for this configuration, member 104 may take any of a variety of cross-sectional shapes, for example, rectangular, elliptical, or the like. While sleeve 102 of this embodiment differs from that of the other embodiments, one skilled in the art shall appreciate, sleeve 102 may be used with member 104 of the first embodiment, just as sleeve 102 of the first embodiment has equal application for this second embodiment. To this end, wire 106 may have a round cross-section or any of a plurality of other predetermined shapes, for example, triangular, to engage pre-formed, complementary threads formed on an outer periphery, distal portion of member 102.

Figure 7A:
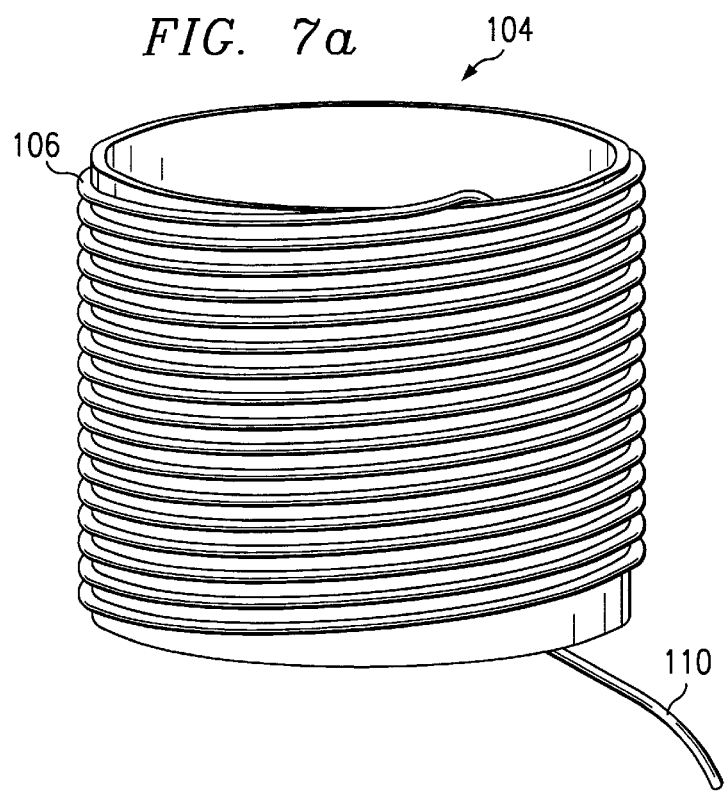
FIGS. 7a and 7b are perspective views of filament windings for the ligating band dispensers of FIGS. 6a and 6b.
Figure 7B:
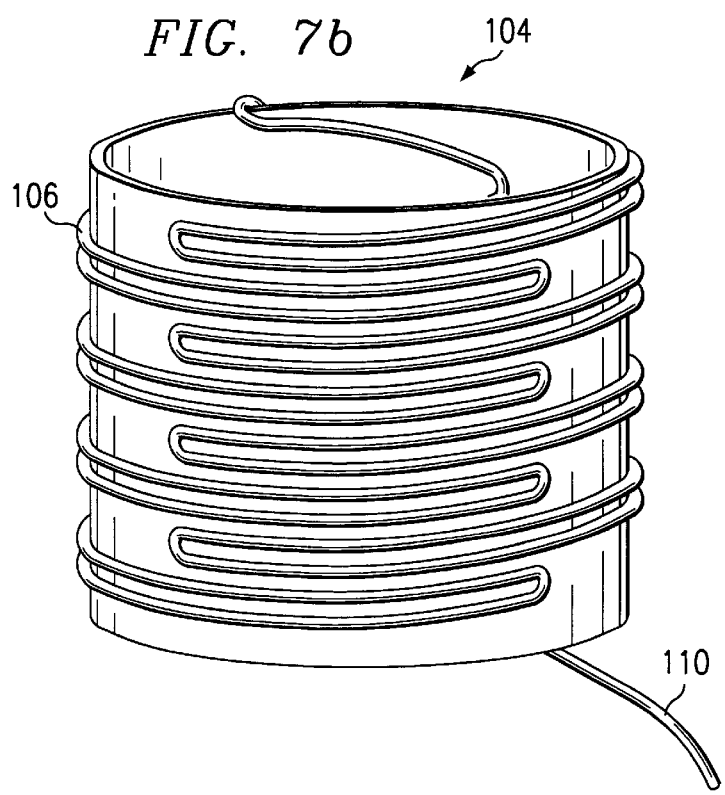

The first embodiment and the second embodiment are illustrated as having a simple helical filament/wire winding (for example, the winding of FIG. 7a). One skilled in the art shall appreciate, however, other windings may be used to achieve specific dispensing control. To this end, FIG. 7b illustrates but one example of a series of non-helically wound loops.

For members 104 of FIGS. 6a and 6b, unwinding filament/wire 106 may produce foundation/adhesive fragments which are consequently passed into a patient's system. While there is likely no harm to the patient given the non-reactive nature of the bonding material, a user may desire to avoid the introduction of such material into a patient's body. Accordingly, the third and the fourth embodiments are provided which minimize the use of adhesives or other bonding agents to form member 104.

Referring to FIG. 6c, the third embodiment features an interlocking member 106 which, when joined, forms self-disposing member 104. More specifically, member 106 has a male portion 106a and a female portion 106b, which enables each winding to engage adjacent windings. Male portion 106a and female portion 106b may assume any cross-sectional shape conducive to mating and forming an engaged interrelationship, for example, an elliptical cross-section (as illustrated in FIG. 6c), rectangular, circular, or the like. Member 106 may be formed from any suitable medical grade material, whether metal, a polymer, or other like materials.

When member 104 is formed, the female portion 106b should grasp male portion 106a of an adjacent winding with sufficient strength to allow member 104 to travel along sleeve 102, without disengaging, despite carrying one or more expanded ligating bands 50 which each apply a constrictive circumferential force. If female portion 106b cannot be formed to provide this engaging strength, a small quantity of adhesive or the like may be used to bond each winding to adjacent windings. Whether bonded or not, aperture 103 assists in effecting the disengagement of interlocking member 106 from adjacent windings during a dispensing operation.

As FIG. 6c illustrates but one example, other conventional mechanical bonding techniques, such as hook and loop, a zipper, friction interlock, as well as others, may be used to join successive windings and are contemplated by the present invention.

FIG. 6d illustrates a fourth embodiment of dispenser 100. Member 104 is a unitary, cylindrical body formed from a medical grade polymer, fiber-reinforced material, thin metal, or the like. Member 104 is subject to a secondary process, for example, a continuous helical cut or an intermittent helical cut (i.e., perforations), to allow member 104 to be unwound when free portion 110 is proximally displaced.

Helical path 106a is cut into the surface of original member 104, wherein the cut does not preferably extend completely through the material of member 104. Alternatively, member 104 could be spirally severed and the windings of member 104 reattached using an adhesive prior to positioning one or more ligating bands 50 thereon, or the material from which member 104 is formed may possess such rigidity so as not to require reattachment. For this latter variation, of course, the material must necessarily retain sufficient flexibility to allow member 104 to be unwound. As a further alternative, member 104 may be formed or molded to include one or more substantially helical, thin-wall portions to facilitate the unwinding of member 104 in a manner consistent with that illustrated in FIG. 6*d*.

Sleeve 102 of the fourth embodiment is shown to include shoulder 116. Optionally joined to sleeve 102, shoulder 116 functions to prevent member 104 from prematurely separating from sleeve 102 during a ligating band dispensing operation. Shoulder 116 may extend about member 102 continuously or intermittently. Shoulder 116 may have equal function with regard to member 102 of at least the embodiments of FIGS. 6*a* and 6*c*. To ensure member 104 is properly positioned relative to sleeve 102, member 104 may be biased distally against shoulder 106 by, for example, a control filament (not shown) or a spring (not shown).

As briefly mentioned above, free portion 110 of member 106 for each of the above embodiments terminates at control portion 12 of a hosting endoscope 10. A proximal end of free portion 110 may be engaged by a controller (not shown) to automatically effect the proximally-directed displacement for a dispensing operation. Alternatively, a user may effect a dispensing operation through application of a manual, proximally-directed displacement. For such operation, free portion 110 may include visible markers or the like (not shown) to indicate a proximally drawn distance necessary to effect dispensing of a ligating band 50.

For each of the embodiments above, sleeve 102 supports member 104; however, sleeve 102 is optional. Member 104 may extend from insertion tip 16 of a hosting endoscope 10, where the inner periphery of member 104 defines a volume to accept that tissue targeted for ligation otherwise defined by sleeve 102. As discussed at length above, with sleeve 102, members 104 advances distally as unwound to effect dispensing of carried ligating bands 50. Without sleeve 102, member 104 simply decreases in length as unwound.

For the above examples, ligating band dispenser 100 is shown to be fixed on an insertion tip 16 of a hosting endoscope 10. As an alternative embodiment, dispenser 100 may be adapted to move relative to an insertion tip 16 of a hosting endoscope 10 and controlled in accordance with that disclosed within co-pending application, Ser. No. 09/062, 281, filed Apr. 17, 1998.

Ligating band dispenser 100 may be further used with an endoscope, as illustrated in the above examples, or manufactured or included as part of a dedicated ligating instrument (not shown).

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A ligating band dispenser, comprising a generally tubular self-disposing member, having an outer surface suitable to support at least one ligating band,
    wherein the self-disposing member is constructed so that during a dispensing operation at least a portion of said member is separated from a remaining portion of said member and said outer surface is reduced.

2. A ligating band dispenser in accordance with claim 1, wherein the member is operatively disposed to yield at least a single linear element during a dispensing operation.

3. A ligating band dispenser in accordance with claim 1, wherein an element, which forms the member, is adapted to at least partially tear away from the member during a dispensing operation.

4. A ligating band dispenser in accordance with claim 1, wherein a portion of an element, such element forming at least in part the member, is adapted to break free, during a dispensing operation, from at least one bond that joins the portion of the element to another, adjacent portion of the element.

5. A ligating band dispenser in accordance with claim 4, wherein a bond is formed from an adhesive.

6. A ligating band dispenser in accordance with claim 4, wherein a bond is formed from a substantially unitary coating.

7. A ligating band dispenser in accordance with claim 4, wherein a bond is formed from a weld.

8. A ligating band dispenser in accordance with claim 4, wherein a bond is formed from a mechanical interlocking connection between the element and the member.

9. A ligating band dispenser in accordance with claim 1, wherein a portion of an element, such element forming at least in part the member, is adapted to be freed, during a dispensing operation, from another, adjacent portion of the element along a disposing path.

10. A ligating band dispenser in accordance with claim 9, wherein the disposing path is spiral.

11. A ligating band dispenser in accordance with claim 9, wherein the disposing path is non-spiral.

12. A ligating band dispenser in accordance with claim 9, wherein the disposing path is defined by at least one pre-defined void.

13. A ligating band dispenser in accordance with claim 9, wherein the disposing path is defined by adjacent surfaces of a spirally wound filament which at least partially forms the self-disposing member.

14. A ligating band dispenser in accordance with claim 9, wherein the disposing path is defined by a region of the member having a reduced strength relative to other regions of the member.

15. A ligating band dispenser in accordance with claim 1, wherein an axial length of the self-disposing member is reduced during a dispensing operation.

16. A ligating band dispenser in accordance with claim 1, further comprising a tubular inner member to receive and be at least partially encompassed by the self-disposing member.

17. A ligating band dispenser in accordance with claim 16, wherein an inner periphery of the self-disposing member defines a substantially threaded surface, and an outer periphery of the inner member has a surface which complements and at le ast partially engages the threaded surface of the self-disposing member when the self-disposing member is operatively positioned relative to the inner member.

18. A ligating band dispenser, comprising a self-disposing member formed of a spirally wound element,
    wherein an outer periphery defined by the spirally wound element is suitable to support at least one ligating band, and wherein the outer periphery of the member is operatively subject to diminishment as the element is unwound.

19. A dispenser in accordance with claim 18, wherein the element is a filament.

20. A dispenser in accordance with claim 19, further comprising a bonding material, wherein the element is positioned at least partially within the material to form a substantially unified body.

21. A dispenser in accordance with claim 18, wherein the member is a wire coil.

22. A dispenser in accordance with claim 18, wherein the element defines a protrusion and a recess, wherein the recess complements a shape of the protrusion.

23. A dispenser in accordance with claim 22, wherein the protrusion and the recess are oppositely positioned, and when the element is spirally wound, the element releasably engages adjacent windings.

24. A dispenser in accordance with claim 18, wherein each winding of the spirally wound element is joined to an adjacent winding.

25. A dispenser in accordance with claim 24, wherein each winding is joined to the adjacent winding with a portion of material of the element, wherein the portion of material is weaker relative to the material of the element and will allow a prescribed separation of each winding from a proximal winding during a dispensing operation.

26. A dispenser in accordance with claim 18, wherein the element terminates in a free portion, and the free portion allows control of the member to effect dispensing of at least one supported ligating band from a distal end of the member.

27. A dispenser in accordance with claim 18, further comprising an inner member which receives the self-disposing member.

28. A dispenser in accordance with claim 27, wherein the element interfaces with the inner member to control axial movement of the self-disposing member during a dispensing operation.

29. A dispenser in accordance with claim 27, wherein the inner member includes a retaining member to maintain the self-disposing member in a predetermined position when the self-disposing member is operatively positioned relative to the inner member.

30. A ligating band dispenser, comprising:
 a self-disposing member having a unitary body which is adapted to support at least one ligating band; and
 a support member which receives the self-disposing member,
 wherein the self-disposing member is formed as a spirally wound element, and the element is wound to enable distal advancement of the self-disposing member relative to the support member during unwinding.

31. A dispenser in accordance with claim 30, wherein the element is a filament, and each winding of the element is joined to an adjacent winding with a bonding material in which the element is set.

32. A dispenser in accordance with claim 30, wherein the member is a wire coil.

33. A dispenser in accordance with claim 30, wherein the element has a male portion and an oppositely positioned female portion, wherein the female portion complements the male portion.

34. A dispenser in accordance with claim 33, wherein when the element is spirally wound to form the member, the female portion of the element releasably engages the male portion of an adjacent winding.

35. A dispenser in accordance with claim 30, wherein the unitary body has at least one thin-wall portion which is spirally arranged about the member and enables a prescribed element winding to be separated from an adjacent winding during a dispensing operation.

36. A dispenser in accordance with claim 30, wherein the element terminates in a free portion, and the free portion allows control of the member to effect dispensing of at least one supported ligating band from a distal end of the member.

37. A dispenser in accordance with claim 30, wherein the element interfaces with the inner member to control axial movement of the member during a dispensing operation.

38. A method of ligating tissue, comprising the steps of:
 positioning a ligating band dispenser, supporting at least one expanded ligating band, on a distal end of an insertion portion of an endoscope, said dispenser including a self-disposing member formed of a wound element that defines an outer periphery to support the at least one expanded ligating band;
 inserting the insertion portion, including the dispenser, within a patient;
 navigating the insertion portion to a desired tissue site;
 adjacent to the tissue site, drawing that tissue to be ligated within a volume defined by the dispenser; and
 controlling the self-disposing member to effect an unwinding of the self-disposing member sufficient to dispense a ligating band.

39. A ligating band dispenser, comprising a generally tubular self-disposing member, having a unitary outer surface suitable to fully support at least one ligating band, wherein the self-disposing member is constructed so that during a dispensing operation the self-disposing member is at least partially consumed to diminish the outer surface.

* * * * *